United States Patent [19]

Green

[11] 4,242,902
[45] Jan. 6, 1981

[54] SURGICAL CLIP APPLICATOR

[75] Inventor: David T. Green, Norwalk, Conn.

[73] Assignee: United States Surgical Corporation, Norwalk, Conn.

[21] Appl. No.: 905,030

[22] Filed: May 11, 1978

Related U.S. Application Data

[63] Continuation-in-part of Ser. No. 843,063, Oct. 17, 1977, Pat. No. 4,152,920.

[51] Int. Cl.³ .................... B21D 9/08; A61B 17/10
[52] U.S. Cl. .................................... 72/410; 128/325
[58] Field of Search .............. 72/410, 409; 128/325, 128/334 R, 335, 346; 227/19; 29/243.56

[56] References Cited

U.S. PATENT DOCUMENTS

| | | | |
|---|---|---|---|
| 2,968,041 | 1/1961 | Skold | 128/335 |
| 3,047,874 | 8/1962 | Kelsey | 72/410 |
| 3,232,089 | 2/1966 | Samuels | 72/410 |
| 3,427,852 | 2/1969 | O'Loughlin | 72/410 |
| 3,439,523 | 4/1969 | Wood | 72/410 |
| 3,463,156 | 8/1969 | McDermott | 128/325 |
| 3,631,707 | 1/1972 | Miller | 72/410 |
| 3,732,719 | 5/1973 | Pallotta | 227/19 |
| 3,777,355 | 12/1973 | Cooke | 29/343.56 |
| 3,777,538 | 12/1973 | Weatherly | 128/325 |
| 3,818,573 | 6/1974 | Scatto | 72/410 |
| 3,837,555 | 9/1974 | Green | 227/19 |
| 3,856,016 | 12/1974 | Davis | 128/325 |
| 3,867,944 | 2/1975 | Samuels | 128/325 |
| 3,924,629 | 12/1975 | Akiyama | 128/325 |
| 3,945,238 | 3/1976 | Eckert | 72/410 |
| 3,954,108 | 5/1976 | Davis | 128/325 |

FOREIGN PATENT DOCUMENTS 1452185 10/1976 United Kingdom .................... 128/325

OTHER PUBLICATIONS

Publication of the United States Surgical Corporation entitled "Stapling Techniques in General Surgery", title page, contents page, and pp. 6, 100 and 101, copyright 1974.

Primary Examiner—Francis S. Husar
Assistant Examiner—Gene P. Crosby
Attorney, Agent, or Firm—Fleit & Jacobson

[57] ABSTRACT

An improved surgical device for applying a clip to a blood vessel or other body tissue, and including a novel clip stop for preventing rearward movement or displacement of the clip, is disclosed. The apparatus of the invention comprises an elongated plate-like or arm member that, in a preferred embodiment, includes means defining a pair of projections and a concave intermediate portion that prevents the rearward movement or displacement of the clip and which serves to cause the elongated plate or arm to be moved upwardly and out of the way upon the actuation of the clip applicator. The device of the invention is particularly suitable for use in combination with surgical clip applicators of the so-called magazine or cartridge type. A particularly advantageous and preferred embodiment includes a novel clip stop assembly of the invention in combination with the unique surgical applicator of U.S. patent application Ser. No. 843,063, now U.S. Pat. No. 4,152,920.

8 Claims, 20 Drawing Figures

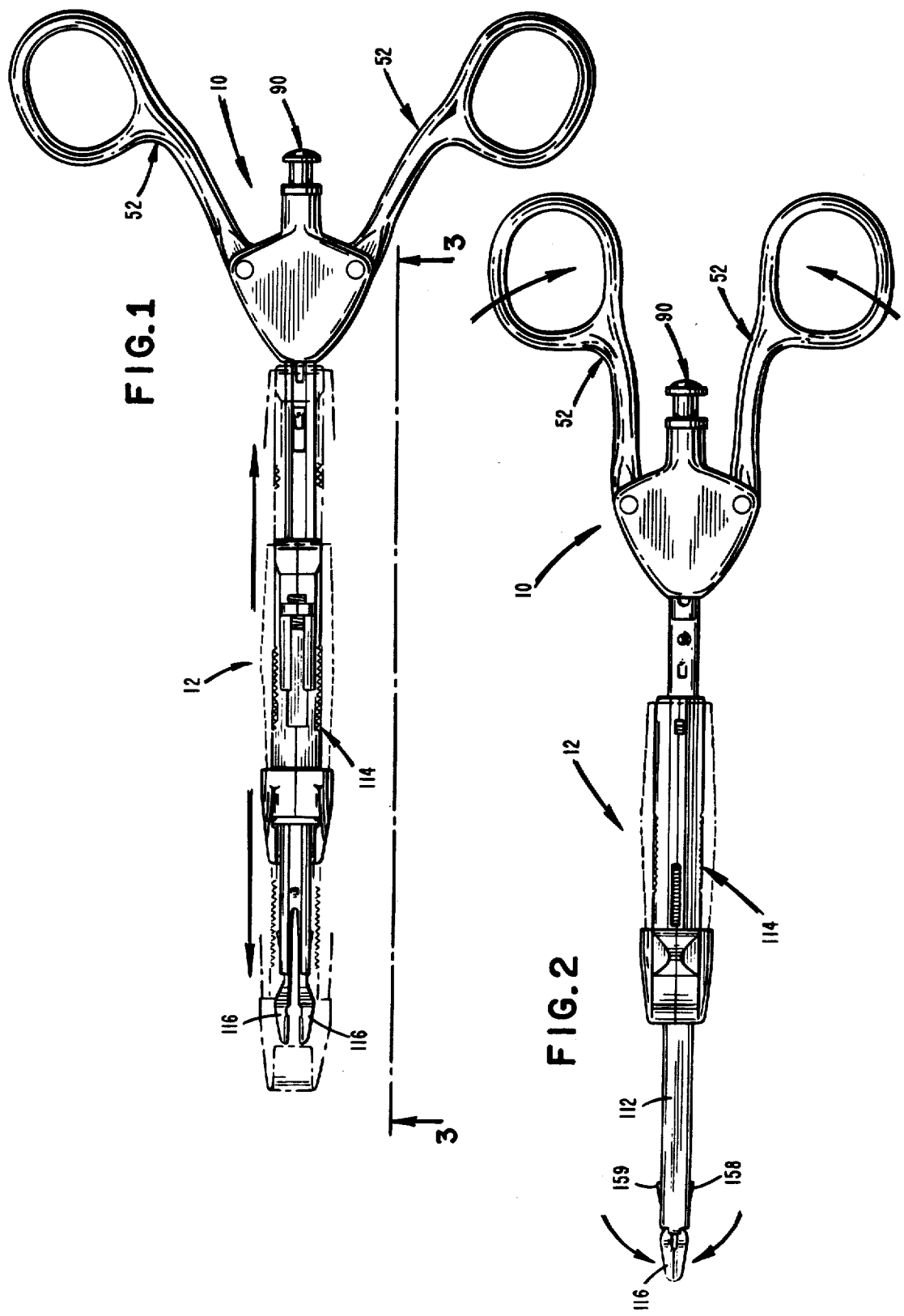

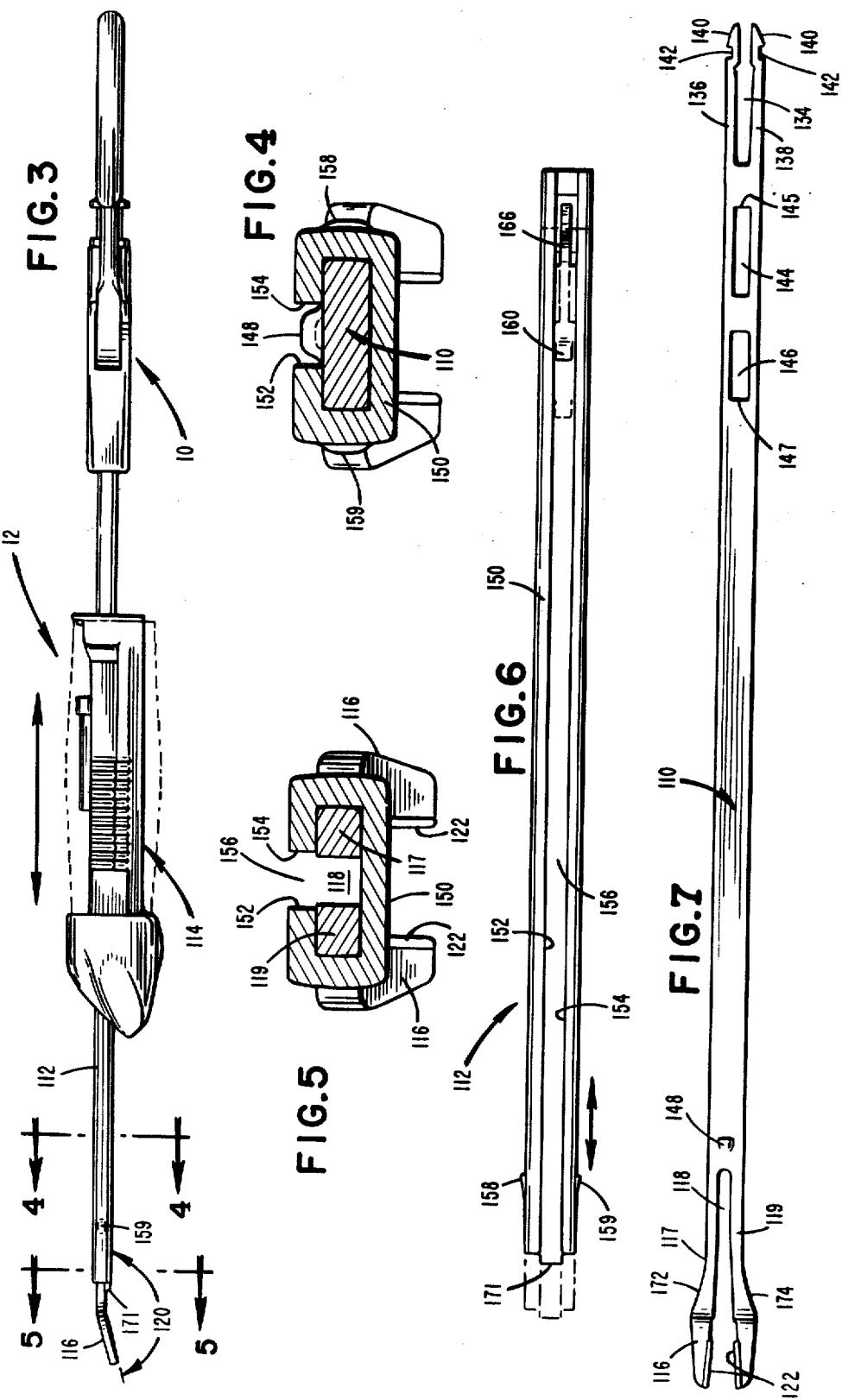

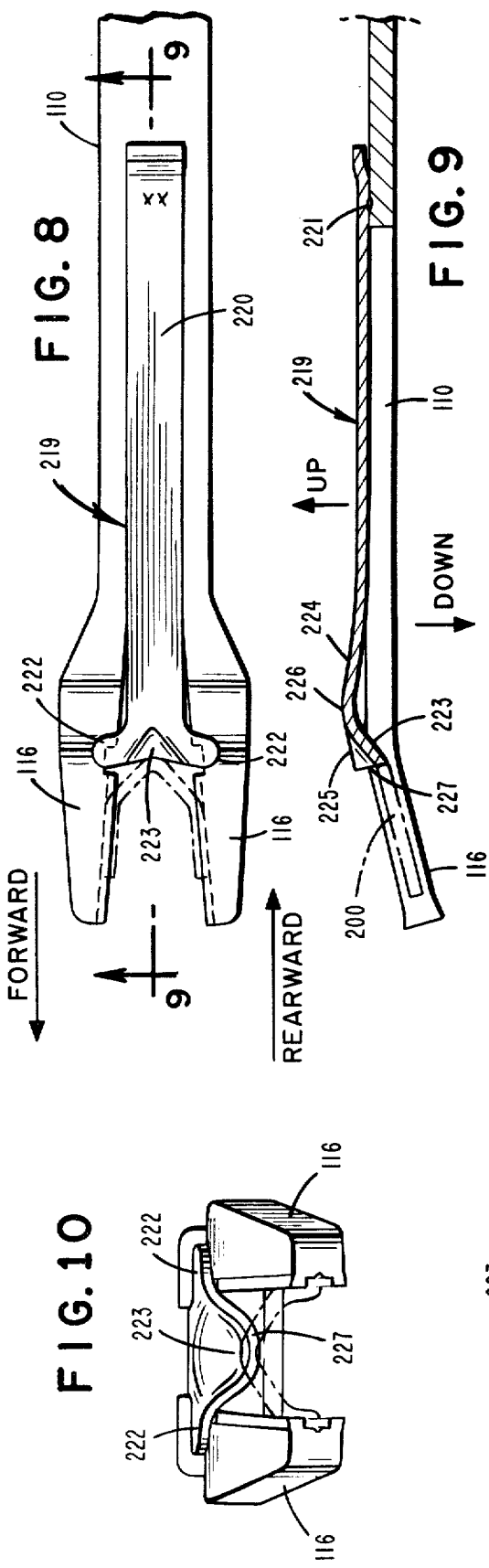
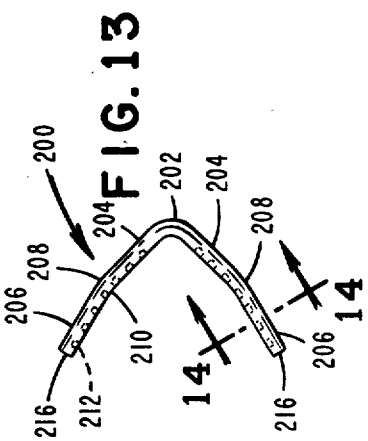
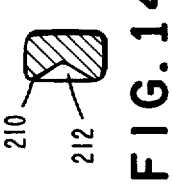
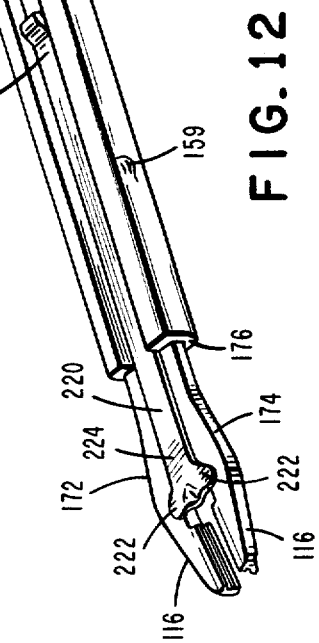
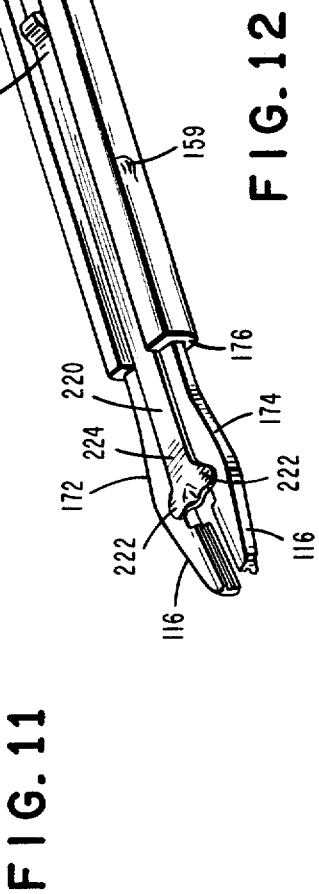

{{ ## 4,242,902 ## }}

SURGICAL CLIP APPLICATOR

RELATIONSHIP TO CO-PENDING APPLICATIONS

The present application is a continuation-in-part of U.S. patent application Ser. No. 843,063, filed Oct. 17, 1977, now U.S. Pat. No. 4,152,920, issued May 8, 1979.

BACKGROUND OF THE INVENTION

1. Field of the Invention

The present invention relates to surgical instruments and, more particularly, to an improved surgical device for applying a clip to a blood vessel or other body tissue.

2. Description of the Prior Art

In recent years, prior artisans have proposed a number of surgical clamp applicators for applying a clip to a blood vessel or the like, and which include a cartridge or magazine capable of holding a sufficient number of surgical clips to accommodate the vessel-restricting requirements of most operations and of releasing the clips, one at a time, successively as required. Specific examples of surgical instruments which utilize or include a cartridge or magazines are disclosed in U.S. Pat. Nos. 2,968,041; 3,232,089 and 3,777,538. In this regard, a further and particularly advantageous surgical applicator of the magazine or cartridge type is disclosed in U.S. patent application Ser. No. 843,063, filed Oct. 17, 1977, and entitled "System for Applying Surgical Clips."

In summary, in accordance with the teachings of the aforesaid patent application, there is provided a novel surgical instrument for applying surgical clips which comprise a primary instrument member and a disposable cartridge which together create a forceps with the cartridge being quickly detachable from the instrument to permit easy and rapid replacement thereof during a surgical procedure. The instrument includes ring handles which act as a forceps and operate to reciprocate a driver. The cartridge includes clinching jaws and a clip magazine with the jaws being quickly detachably connected to the instrument in a fixed manner whereas an actuator sleeve for the jaws is quickly detachably fixed to the reciprocal driver of the instrument. A number of surgical clips can quickly and successively be supplied to the clinching jaws of the cartridge.

While devices such as disclosed above are known, in the operation thereof the clip can be pushed out of position and, in fact, even out of the jaws of the applicator itself upon the application of the clip to a blood vessel or the like. This is particularly true when the instrument and clip are too vigorously or forcefully applied against the tissue. The present invention overcomes this defect of such surgical instruments.

SUMMARY OF THE INVENTION

In summary, the present invention relates to a novel mechanism, hereinafter sometimes referred to as a clip stop, which prevents the clip from moving rearwardly as it is applied to a blood vessel or other body tissue. While the invention may be employed in connection with the varying designs of above-noted surgical applicators, the apparatus of the present invention has particular utility for use in combination with the surgical instrument disclosed in U.S. patent application Ser. No. 843,063, now U.S. Pat. No. 4,152,920.

In the practice of the invention, and broadly speaking for the moment, the clip is prevented from moving rearwardly and is securely held in position until the jaws are actuated and the clip closed about the tissue. The novel structure of the invention comprises an elongated plate-like arm or member having one end fixedly secured to the instrument. In a preferred embodiment, the plate-like stop member comprises resilient means which, as to be discussed in detail hereinbelow, are adapted to be engaged and urged within the opening formed by a pair of opposing spaced-apart jaw members, the latter comprising a primary component part of the surgical applicator itself. The design of the clip stop is such that the actuation of the closing of the jaws moves the resilient stop member upwardly and out of the way. The unique structure of the invention is simple in design and detail and very effectively prevents the clip from unwanted rearward movement, and thus solves a particularly significant problem in this industrial art.

It is accordingly a general object of the present invention to provide an improved surgical clip applicator having means to restrain the clip against rearward movement that might be caused by applying the instrument and clip too vigorously or forcefully against a vein, artery, or other body tissue.

Yet, another object of the invention is to provide a novel surgical clip applicator of the magazine or cartridge type which includes resilient clip restraining means for preventing the clip from rearward movement, and which is very simple in its design and construction, yet is highly effective in its intended function.

BRIEF DESCRIPTION OF THE DRAWINGS

The manner in which the foregoing and further objects are achieved in accordance with the present invention will be better understood in view of the following detailed description and accompanying drawings and wherein:

FIG. 1 is a top plan view of a particularly advantageous arrangement of apparatus that may be used in combination with the unique clip stop mechanism of the present invention.

FIG. 2 is a view similar to FIG. 1 except showing the novel clip applicator with its ring handles closed together and the cartridge with its clinching jaws closed together.

FIG. 3 is a side view of the instrument and cartridge of FIG. 1.

FIG. 4 is a view in section taken along lines 4—4 of FIG. 3.

FIG. 5 is a view in section taken along lines 5—5 of FIG. 3.

FIG. 6 is a view in top plan of the wrap or sleeve component of the disposable cartridge.

FIG. 7 is a view in top plan of the jaw blade component of the disposable cartridge assembly.

FIG. 8 is a top plan view of the jaw blade and jaws in combination with the unique clip stop of the present invention.

FIG. 9 is a longitudinal section taken along lines 9—9 of FIG. 8.

FIG. 10 is a front end view of the embodiment illustrated in FIG. 8.

FIG. 11 is a view similar to FIG. 10 with the jaws in the closed position and the clip stop cammed to a raised position.

FIG. 12 is a perspective view of the embodiment shown in FIG. 8 with the jaw blade being mounted within the sleeve or wrap shown in FIG. 6.

FIG. 13 is a side view of a surgical clip that may be used in combination with the surgical instrument assembly illustrated in FIGS. 1-3.

FIG. 14 is a view in section of FIG. 13 taken along lines 14—14.

DETAILED DESCRIPTION OF PREFERRED EMBODIMENT(S)

Figure 15A:
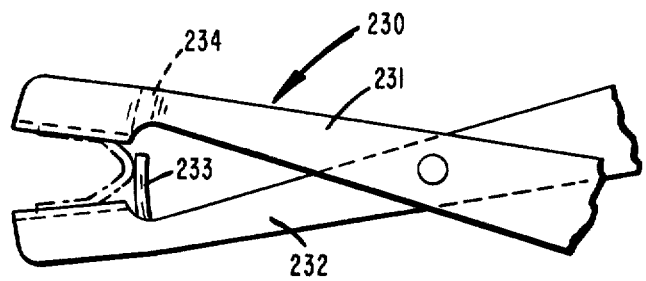
FIGS. 15A, 16A and 17A are side elevational views illustrating further apparatus embodiments of the novel clip stop of the invention.
Figure 15B:
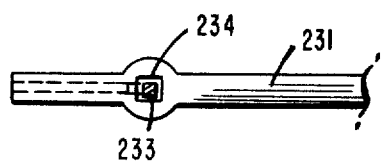
FIG. 15B is a top-plan view of the embodiment shown in FIG. 15A.
Figure 16A:
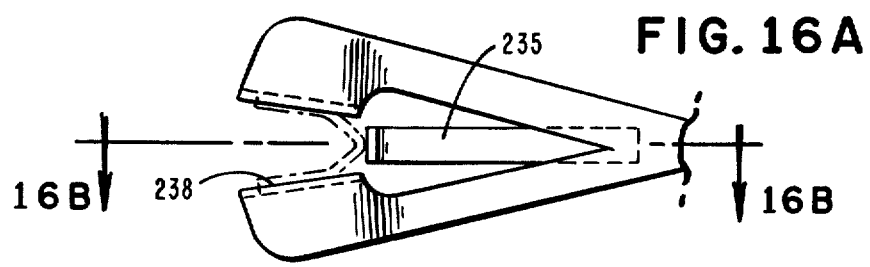
Figure 16B:
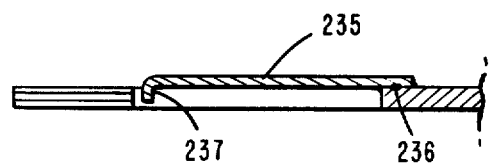
FIG. 16B is a view in section taken along lines 16B—16B of FIG. 16A.

As briefly noted above, the present invention relates to a surgical instrument or applicator wherein a clip is applied to a vein or artery and, more particularly, to a surgical instrument of the magazine or cartridge type which is adapted to hold a number of surgical clips and to release the clips, one at a time, as required for application purposes. In more detail, the present invention relates to novel clip restraining means which prevents the unwanted rearward movement of the clip after the latter has been inserted into the jaws of the applicator.

As will be apparent from the following detailed description, the unique structure of the present invention may be readily adapted and incorporated for use in connection with surgical clip applicators of varying designs. In this regard, however, the present invention has particular utility for use in combination with the novel clip applicator disclosed in U.S. patent application Ser. No. 843,063, filed Oct. 17, 1977, now U.S. Pat. No. 4,152,920. For convenience, and in order to properly define a preferred embodiment, the following details of the present invention are disclosed in combination with the details of the aforenoted patent application Ser. No. 843,063, now U.S. Pat. No. 4,152,920. While the present invention is illustrated and described in terms of this specific preferred embodiment, it should nevertheless be expressly understood that same is intended to be only a means to demonstrate the generic concept of the invention. Such generic concepts are framed and drafted in the claims appended to this specification.

Turning now to the drawings in detail and, first, with reference to FIGS. 1 and 2, there is shown the surgical clip applicator of U.S. patent application Ser. No. 843,063, now U.S. Pat. No. 4,152,920 which comprises an instrument 10 and a detachably mounted disposable cartridge indicated at 12. The specific details of the instrument assembly 10 are disclosed in the aforesaid patent application at pages 8-11 and particularly with reference to FIGS. 9-17 thereof. Such details being deemed to be incorporated herein by reference. For the purposes of the present disclosure, it should only be noted in connection with the instrument assembly 10 that, upon the actuation of the ring handles 52, i.e., by simply drawing them together as shown by the arrows in FIG. 2, the actuator sleeve 112 is caused to be advanced relative to the housing 20, as illustrated generally in FIGS. 1-3.

With reference now to FIGS. 2-7, the quick detachable disposable cartridge 12 comprises a jaw blade 110, shown in FIG. 7, a sleeve 112, shown in FIG. 6, and a cartridge housing assembly generally indicated by the reference numeral 114. The jaw blade 110 is fabricated with a pair of opposing jaws 116 at one end by means of slot 118 defining legs 117 and 119. The jaws 116 are bent out of the plane of the jaw blade 110 which, as indicated at 120, define an angle of approximately 165°.

A pair of longitudinally extending flanges 122 project from the edges of each jaw 116 as shown, e.g., in FIG. 7. The flanges 122 define a groove 123 shown in FIG. 11. The jaw blade 110 is also bifurcated at its other end by means of slot 134 to form legs 136 and 138. The end of each leg is provided with an inclined outer edge 140, which terminates at a recess 142. The legs 136 and 138 have resiliency and can flex towards each other from the reposed position shown in FIG. 7. Rectangularly shaped slots 144 and 146 are also provided in jaw blade 110.

The sleeve 112 of the cartridge assembly comprises an elongated wrap that is formed into a box 150 with the edges 152 and 154 left spaced apart to define a slot 156. A pair of ears 158 and 159 are formed on opposite sides of the box 150 near one end as shown in FIG. 6. As illustrated in FIGS. 1-5, the jaw blade 110 and sleeve 112 are assembled together for relative sliding motion. When assembled, the jaw blade 110 fits within the box structure of the sleeve or wrap 112, as shown in FIGS. 4 and 5. The legs 117 and 119 of the jaw blade 110 are formed with inclined edges or surfaces 172 and 174 which coact with the end 176 of wrap or sleeve 112 as best shown in FIG. 12. When the sleeve 112 is advanced relative to jaw blade 110, by being moved in the direction of the jaws 116, the edge of end 176 engages the inclined surfaces 172 and 174 of jaw blade 110 forcing the jaws 116 to close together.

The jaw blade 110 is inserted into the instrument 10 by introducing legs 136 and 138 into the housing 20 in the manner as disclosed in U.S. Ser. No. 843,063, now U.S. Pat. No. 4,152,920.

As briefly noted above, the instrument is actuated by closing the handles 52 together in the manner best demonstrated in FIG. 2. The closing of the handles serves to advance the actuator rod (not shown) of the instrument in the direction of the arrow in FIG. 2. It should be noted that the jaw blade 110 is stationary relative to the instrument and the advancement of the actuator rod only carries with it the wrap or sleeve 112. During this advancement, the forward edge 176 of the sleeve 112 contacts the inclined surfaces 172 and 174 of legs 117 and 119 to cam jaws 116 to a closed position as illustrated in FIG. 2.

The cartridge housing assembly 114 is slidably mounted or carried on the sleeve 112. Again, it may be noted that the action of the cartridge housing assembly 114 and its structure are described in detail in U.S. Ser. No. 843,063, now U.S. Pat. No. 4,152,920 but, for purposes of this disclosure, it may be simply stated that the cartridge housing assembly 114 is carried on the 112, and is free to slide from a position where it contacts projection 162 on sleeve 112 and to where it contacts ears 158 and 159 on sleeve 112.

When a disposable cartridge has been fully used or consumed, it is ejected from the instrument and discarded.

The clip as used in accordance with the teachings of U.S. Ser. No. 843,063, now U.S. Pat. No. 4,152,920 is illustrated in FIGS. 13 and 14 and comprises a small wire 200 rectangular in cross section with rounded corners bent into a substantial V-shape having an apex bend 202, straight extending inner legs 204 and outer legs 206, which are integrally formed with legs 204. A slight bend 208 defines an angle between the legs sections 204 and 206 of from about 160° to about 175°. The inner surface 210 of the clip 200 is provided with a plurality of V-shaped grooves 212 which are cut or pressed transversely of the surface 210.

Turning now to the specific details of the present invention and with reference first to FIGS. 8 and 9, the inventive clip stop is shown generally as 219. An elongated resilient plate or arm-like member 220 is fixedly secured to the jaw blade 110, as by a spot weld, shown at 221. As illustrated in the drawings, the width of the elongated member 220 is such that it fits within the slot 156 formed by the side edges 152 and 154 of the sleeve or wrap 112. While this width is not critical, it should be such that it does not interfere (as contacting the sidewalls 152 and 154) with the relative sliding motion between the jaw blade 110 and sleeve 112.

In accordance with the present invention, the forward end of the clip stop 219 includes, and is defined by, a pair of oppositely directed projections or ears 222 and concave or V-shaped, intermediate portion 223. As best illustrated in FIGS. 9 and 12, the forward end of the clip stop 219 includes an upwardly directed flared portion 224 and an oppositely and/or downwardly directed portion 225. In other words, the forward end of the arm 220 is bent at 226 so that the V-shaped intermediate portion is, when the jaws 116 are in an open position as shown in FIG. 8, caused to be urged downwardly in a manner such that forward end 227 of the intermediate portion 223 projects within the sidewalls or flanges 122 of the jaws 116. This is best shown in FIGS. 9 and 10. In this manner, and as should be readily apparent, the clip (200) is very effectively prevented from an unwanted rearward movement, even when the instrument and clip are forcefully urged against the tissue or blood vessel.

As the jaws 116 are closed as described above, the projection or ears 222, which in a jaw-open position press against the upper surface of the jaws, are caused to be cammed upwardly, as best illustrated in FIG. 11, so that the forward end 227 of the clip stop 219 is out of the way. In other words, the design of the novel clip stop of the invention is such that the closing of the jaws moves the clip stop upwardly and out of the way. Thus, the unique clip stop, while very effectively preventing rearward movement or displacement of the clip 200, does not interfere with the functional aspects of the applicator itself.

In assembling the clip stop of the invention, the plate-like member or arm 220 is simply placed in position, i.e., over the slot 118 with the forward end thereof being placed as shown in FIG. 9, and is then secured to the jaw blade 110 as by spot welding at 221. The material of construction of the clip stop should be that of the clamp applicator itself with the use of stainless steel being particularly preferred and advantageous. As should be apparent to those skilled in the art, the present invention is simple in design and construction, is very reliable in operation and further provides a truly remarkable solution to a problem associated with known surgical clamp applicators. While the invention has been disclosed, in a preferred embodiment, for use in combination with the surgical device of U.S. Ser. No. 843,063, now U.S. Pat. No. 4,152,920 which is deemed to be incorporated in its entirety herein by reference, the underlying generic concept of the invention may, of course, be employed for use in combination with surgical clamp applicators of varying designs, whether of the cartridge type or not. It should also be understood that the design of the clip stop may differ from the above-disclosed embodiments without departing from the generic concept of the invention.

In this regard and with reference now to FIGS. 15A–17B, there is shown further known surgical clip applicators in combination with varying designs of the clip stop of the invention. Thus in FIG. 15A there is shown a surgical clip applicator 230 which includes a pair of pivotally connected arms 231 and 232. As clearly shown in FIG. 15A, in this embodiment the clip stop, indicated at 233, is formed integrally with the inner surface of the arm 232 and is adapted to pass through an opposed or mating aperture 234 formed in the opposed arm 231. Also note FIG. 15B. In the embodiment of FIGS. 16A and 16B, the clip stop comprises an elongated plate-like member 235 which, as best shown in FIG. 16B, is secured to the clamp applicator at 236. Again as clearly shown in the drawings in FIGS. 16A and 16B, the forward end of the plate-like clip stop 235 is bent downwardly at 237 to form a small shoulder portion that is effective to prevent rearward movement of the clip 238.

Figure 17A:
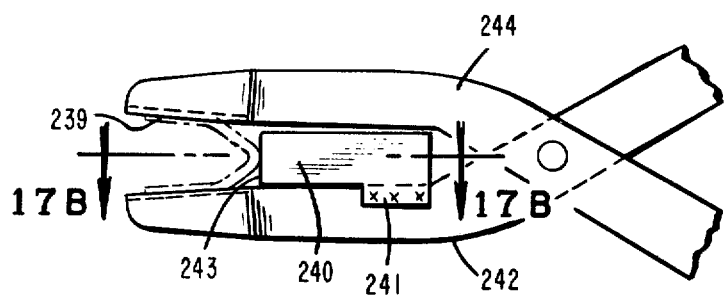
Figure 17B:
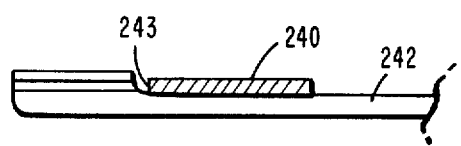
FIG. 17B is a view in section taken along lines 17B—17B of FIG. 17A.

A still further embodiment of the novel clip stop of the invention is shown in FIGS. 17A and 17B. In this embodiment, the clip stop 240 is secured, as by tack welding at 241, to one arm (242) of the surgical applicator. The clip 239 is prevented from any unwanted rearward movement by the forward surface 243 of the clip stop. Note, e.g., FIG. 17B. The arm 244 is in a different plane than that of clip stop 240, the latter thus not interferring with the closing of the opposed arms.

While varying designs of the clip stop have been shown and discussed hereinabove, it should be readily apparent to those skilled in the art that such embodiments have been shown for illustrative purposes only. Thus it should be expressly understood that the disclosed embodiments are not intended to limit the invention thereto and that further embodiments could be employed without departing from the underlying and generic concept of the present invention.

What is claimed is:

1. In an apparatus for applying surgical clips comprising at one end a pair of opposed spaced-apart grooved jaws; means operably associated with said jaws and adapted to contain a plurality of surgical clips and to feed them singly to a predetermined position between said jaws, and means operable to close said jaws to clinch a clip held therein, the improvement comprising a resilient elongated arm member having clip stop means defining a pair of outwardly directed projections and a concave intermediate portion, said intermediate portion serving to prevent rearward movement of said clip.

2. The apparatus in accordance with claim 1 wherein said outwardly directed projections extend above said jaws whereby upon the actuation of the closing of said jaws, said resilient elongated arm member is caused to be moved upwardly and out of the clinching surfaces formed by said jaws.

3. An improved surgical device for applying a clip to a vein, artery or other body tissue and comprising an instrument, a disposable cartridge and a novel clip stop assembly, (1) said cartridge comprising:
  (a) elongated blade means defining at one end a pair of opposed jaws resiliently spaced apart,
  (b) actuation means movable relative to said blade to close said jaws together, and
  (c) cartridge housing means movably mounted on said blade means adapted to contain a plurality of surgical clips and feed them singly to a predetermined position relative to the jaws of said blade means so that movement of cartridge housing means relative to said blade means will transfer the clip in said predetermined position to said jaws properly oriented to be clinched by said jaws, and
(2) said instrument comprising
  (d) a body,
  (e) driver means mounted for movement in said body,
  (f) movable handle means mounted in said body,
  (g) means for translating motion of said handle means into movement of said driver means; and
(3) said clip stop assembly comprising
  (h) a resilient elongated arm member having one end fixedly secured to said elongated blade means of said cartridge,
  (i) clip stop means formed integrally with the opposite end of said elongated arm member and defining a pair of outwardly directed projections and a concave intermediate portion,
    said intermediate portion serving to prevent rearward movement of said clip held by said opposed jaws,
    said outwardly directed projections extending above said jaws whereby upon the actuation of the closing of said jaws, said resilient elongated arm member is caused to be moved upwardly and out of the clinching surfaces formed by said jaws.

4. The apparatus in accordance with claim 3 wherein said instrument further includes ring handles pivotally mounted on said body.

5. An apparatus for applying surgical clips and including an instrument and a disposable cartridge detachably connected thereto, said cartridge comprising
  (a) elongated blade means defining a pair of opposed jaws resiliently spaced apart,
  (b) actuation means movable relative to said blade to close said jaws together,
  (c) cartridge housing means movably mounted on said blade means adapted to contain a plurality of surgical clips and feed them singly to a predetermined position relative to the jaws of said blade means so that movement of cartridge housing means relative to said blade means will transfer the clip in said predetermined position to said jaws properly oriented to be clinched by said jaws, said cartridge adapted to be quick detachably connected to an instrument provided with complimentary components of said quick detachable means, and
  (d) a resilient elongated clip stop mechanism having one end fixedly secured to said elongated blade means and having at its opposite end, stop means defining a pair of outwardly directed projections and a concave intermediate portion, said intermediate portion serving to prevent rearward movement of said clip clinched by said opposed jaws, said outwardly directed projections extending above said jaws whereby upon the actuation of the closing of said jaws, said resilient elongated arm member is caused to be moved upwardly and out of the clinching surfaces formed by said jaws.

6. A novel clip stop adapted for use in a surgical device including a mechanism for applying a clip to a vein, artery or other body tissue, said clip stop comprising an elongated member, means positioned at the forward end of said member to prevent rearward movement of said clip, said means defining opposing outwardly directed projections and an intermediate concave portion, said projections serving to cause said elongated arm member to be moved from, and out of the way of, the mechanism for applying said clip as said clip is caused to be clinched to said vein, artery or body tissue, said concave portion serving to prevent rearward displacement of said clip during its said application to said vein, artery or blood vessel.

7. The apparatus in accordance with claim 6 wherein said intermediate portion is V-shaped.

8. An instrument for applying a surgical clip comprising closable opposed spaced-apart grooved jaws for holding and crimping said surgical clip; a movable clip stop positioned between said jaws when said jaws are open to prevent unwanted rearward motion of said clip whereby the closing of said jaws to crimp said clip causes said movable clip stop to move out from between said jaws so that said jaws may close to completely crimp the clip.

* * * * *